United States Patent [19]
Schwardt et al.

[11] Patent Number: 6,112,122
[45] Date of Patent: Aug. 29, 2000

[54] PREFORMED EXTENDABLE MESH CATHODE FOR IMPLANTABLE BONE GROWTH STIMULATOR

[75] Inventors: Jeffrey D. Schwardt, Morristown; George B. Jankowski, Great Meadows, both of N.J.

[73] Assignee: Electro-Biology, Inc., Parsippany, N.J.

[21] Appl. No.: 09/193,454

[22] Filed: Nov. 17, 1998

[51] Int. Cl.$^7$ .................................................. A61N 1/36
[52] U.S. Cl. ............................................. 607/51; 607/116
[58] Field of Search ................. 607/50, 51, 52, 607/115, 116, 129

[56] References Cited

U.S. PATENT DOCUMENTS

| | | | |
|---|---|---|---|
| D. 365,634 | 12/1995 | Morgan | D24/155 |
| 3,760,812 | 9/1973 | Timm et al. | 607/116 |
| 3,842,841 | 10/1974 | Brighton et al. | 128/419 R |
| 3,964,473 | 6/1976 | Wickham et al. | 128/82.1 |
| 4,506,673 | 3/1985 | Bonnell | 128/419 |
| 4,540,878 | 9/1985 | Sato | 219/545 |
| 4,567,900 | 2/1986 | Moore | 607/129 |
| 4,776,337 | 10/1988 | Palmaz | 128/343 |
| 4,922,905 | 5/1990 | Strecker | 606/195 |
| 5,108,435 | 4/1992 | Gustavson et al. | 623/16 |
| 5,255,692 | 10/1993 | Neubauer et al. | 607/122 |
| 5,304,210 | 4/1994 | Crook | 607/51 |
| 5,330,524 | 7/1994 | Mar | 607/129 |
| 5,360,440 | 11/1994 | Andersen | 607/116 |
| 5,468,242 | 11/1995 | Reisberg | 606/69 |
| 5,695,516 | 12/1997 | Fischell et al. | 606/194 |

OTHER PUBLICATIONS

Black J, Nord DS, Jones SB, Dymecki SM, Baranowski TJ, Brighton CT: The Role of Electrode Maerial and Current Density in Electrical Stimulation of Osteogenesis, 2nd Ann. Oxford, BRAGS, 1982, p. 56.

"SpF™–2T and SpF™–4T Implantable Monitorable Spinal Fusion Stimulators," EBI product literature, P/N 196004 Oct. 1989 (two pages).

"The SpF®–T Spinal Fusion Stimulator: An Efficacious Adjunct that Meets the Diverse Needs of Spine Patients," EBI product literature, P/N 196052, May 1995 (two pages).

"OsteoGen® Surgically Implanted Bone Growth Stimulator, Procedures for Surgical Use," EBI brochure P/N 193069, Dec. 1995.

"When can you use the EBI® OsteoGen™?", EBI product literature, P/N 193076, Mar. 1996 (two pages).

"Introducing SpF®–XL II The New Long–Distance Champ," EBI product literature, P/N 196128, Feb. 1997.

"SpF® Implantable Spinal Fusion Stimulators, Procedures for Surgical Use," EBI brochure P/N 196067, Dec. 1997.

*Primary Examiner*—William E. Kamm
*Attorney, Agent, or Firm*—Woodard, Emhardt, Naughton Moriarty & McNett

[57] ABSTRACT

An implantable bone growth stimulator comprising an electrical signal generator having an anode connected thereto along with a prefabricated flexible wire mesh cathode that is extendable to at least twice its preformed initial length. The cathode in a preferred embodiment includes a single chain of conductive wire links formed as alternating loops and twists of two strands of monofilament titanium wire.

15 Claims, 5 Drawing Sheets

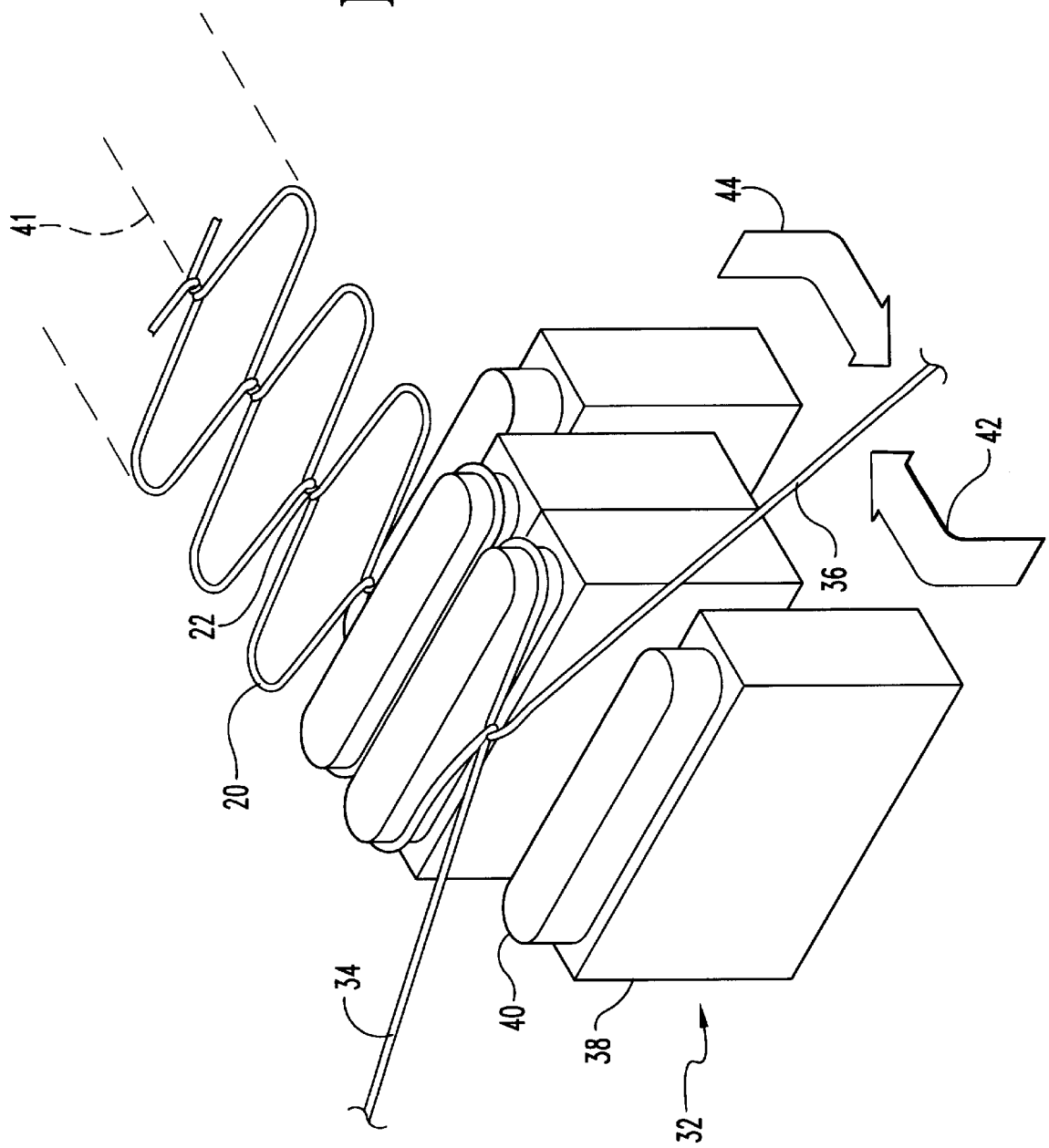

PREFORMED EXTENDABLE MESH CATHODE FOR IMPLANTABLE BONE GROWTH STIMULATOR

BACKGROUND OF THE INVENTION

This application relates generally to bone growth stimulators, and more particularly to electrodes for use with implantable stimulators employing direct current for stimulation of bone growth.

Bone growth stimulators employing direct current are known to be useful as adjuncts to surgical procedures for treatment of poorly healing bone fractures known as nonunions, and as adjuncts to spinal fusion procedures among other applications. Direct current bone stimulation is performed by supplying a constant current to an electronegative cathode implanted at a bony site where fusion is desired. Stimulation of bone growth depends in part on maximal contact between the cathode surface and viable bone at the fusion site, which is normally prepared by debriding or decorticating host bone to expose live bone cells. It is preferable that the cathode contact both the host bone and any graft material placed at the fusion site.

Cathode flexibility, and in particular an ability to conform to the shape of a fusion site, is an important factor affecting the extent of such contact. Other factors include the roughness of the prepared surface of the fusion site, unevenness of the interface between the cathode and graft material packed against it, gaps between bone fragments at a nonunion site, and, in spinal fusion cases, open spaces between vertebrae to be fused together.

The performance of a bone growth stimulator can also be affected by pre-implant manipulations of the cathode by a surgeon or surgical assistant to make it conform to a fusion site. Cathode manipulations vary among surgeons and their assistants and can lead to inconsistent cathode configurations, and thus inconsistent results, from case to case. A cathode requiring little or no manipulation at the time of implantation is desirable, and it would be particularly desirable to have a cathode requiring minimal manipulation for a range of sizes of fusion sites.

Various electrode configurations are known for use in DC bone growth stimulation, including mesh electrodes as well as electrodes having straight, sinusoidal, or helical shapes. A mesh anode, for example, is disclosed in U.S. Pat. No. 3,842,841 to Brighton et al. The anode has a metal face plate 0.7 mm thick to which a stainless steel mesh is soldered. As such, the anode has little if any conformability and cannot be extended in length. U.S. Pat. No. 5,304,210 to Crook discloses a mesh electrode frame placed over a bone injury site for purposes of bone growth stimulation. The mesh is a single rectangular piece of generally flexible material with two rows of apertures formed therein. There is no indication that it is designed to stretch and it appears incapable of stretching.

Mesh cathodes are disclosed along with individual wire cathodes in U.S. Pat. No. 4,506,673 to Bonnell, for use in stimulating tissue growth in cartilage or ligaments. Bonnell refers to cutting or otherwise shaping a cathode to approximate the shape of a defect to be treated, and discusses rolling or folding of a mesh cathode for insertion followed by unrolling of the cathode and arthroscopically guided positioning thereof over the defect to be treated. Stretching of a cathode is not discussed, and the disclosed mesh cathodes, each in the form of a square-cell grid, are incapable of substantial stretching.

Electro-Biology, Inc. (EBI), the assignee of the present invention, manufactures a cathode of trifilar wire, i.e., three-filament stranded wire, designed to be manually shaped by a surgeon at the time of implantation to conform to the surgical site. The trifilar wire is typically manipulated into a zigzag or sinusoidal wave shape or into a helix. A helix may be formed with the aid of a stepped, cylindrical mandrel provided for such purposes, or by directly wrapping the wire cathode around a length of cortical bone graft. The helix configuration is typically placed in a trough or a drill hole extending across a nonunion, but may alternatively be inserted directly into a nonunion site between the bone surfaces to be stimulated. In a spinal application, the helix configuration is known to have been flattened and stretched to fit a desired fusion site.

A trifilar wire cathode with a sinusoidal wave shape for spinal fusion is also available from EBI as a prefabricated cathode, that is, a cathode formed into the desired shape at the time of fabrication. The preformed shape of this prior art cathode is shown in FIG. 2. In the example illustrated, the cathode has 12 cm of trifilar wire formed as shown to create a wave with an area of coverage, or footprint, having a nominal length (L) of 4 cm and a nominal width (W) of 1 cm. This cathode is also available in a 24-cm size having twice as many cycles of the wave as in the 12-cm size, and a footprint twice as long, i.e., 8 cm long. A surgeon adjusts the prefabricated, or factory-preformed, cathode in length to fit the length of a fusion site. The preformed wave shape provides consistency and reduces surgical preparation time, and its efficacy is well documented. Nevertheless, there remains a need for a cathode configuration that further improves the delivery of direct current to a bone fusion site while minimizing pre-implant manipulations.

SUMMARY OF THE INVENTION

The present invention meets the above-stated need and provides advantages over prior art devices with an implantable bone growth stimulation cathode comprising a single, prefabricated, axially extendable chain of conductive wire links, the links each preformed with an axial length less than the width thereof, wherein the chain is extendable to at least twice its preformed length.

In particular, the present invention provides more even coverage of a given area with a given amount of cathode material than is provided by the existing straight or sinusoidal trifilar cathodes described above, and thereby increases the chances of intimate contact with host bone and graft material. The invention also minimizes pre-implant manipulations for a substantial range of sizes of fusion sites.

The preferred geometry of a cathode according to this invention facilitates greater bone contact in a given area of coverage than the sinusoidal wave geometry of the above-referenced trifilar wire cathode, while maintaining the same exposed surface area of the cathode itself and also maintaining comparable electrochemical and mechanical performance characteristics.

According to another aspect of the present invention, an implantable bone growth stimulator includes an electrical signal generator having an anode and prefabricated flexible wire mesh cathode connected thereto, the wire mesh cathode being extendable in length to at least twice its preformed initial length.

It is a general object of this invention to provide improvements in direct current bone growth stimulation devices and methods.

A further object of the invention is to improve the delivery of direct current to a bone fusion site while minimizing pre-implant manipulations.

Yet another object is to provide more uniform distribution of electric current to a fusion site in combination with a cathode capable of being stretched substantially in length.

These and other objects and advantages of the invention will become more apparent upon reading the following detailed description in conjunction with the accompanying drawings.

BRIEF DESCRIPTION OF THE DRAWINGS

FIG. 8 is a perspective view of a mechanism for fabrication of the mesh for a cathode according to the preferred embodiment of the present invention.

DESCRIPTION OF THE PREFERRED EMBODIMENT

Figure 1:
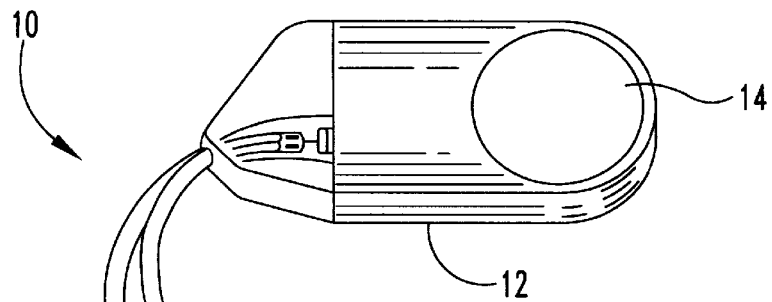
FIG. 1 is an illustration of the preferred embodiment of a bone growth stimulator with mesh cathode according to the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, the preferred embodiment of a bone growth stimulator 10 according to the present invention includes a constant current generator 12, an anode 14 integrally formed on the case of the generator, and one or more mesh cathodes 16 connected to the current generator by respective electrical leads 18. The current generator is designed to maintain a constant DC current of, for example, 10 µA between the anode and each cathode despite wide variations in bone/tissue resistance. The field of influence is approximately 5–8 mm in radius around the cathode wire. Current generator 12 with integral anode 14 may be of the type commercially available from EBI in the OsteoGen™ line of bone growth stimulators or the SpF® line of spinal fusion stimulators. The entire bone growth stimulator is designed to be implanted in a patient's body with the cathodes(s) placed at the desired fusion site(s) and the signal generator placed in subcutaneous tissue 8–10 cm away.

Figure 4:
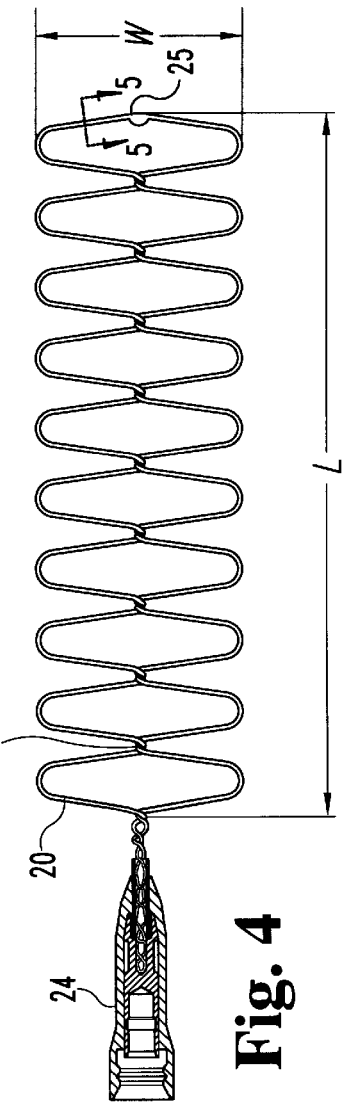
FIG. 4 is a plan view of the preferred embodiment of a mesh cathode according to the present invention.

FIG. 4 shows a mesh cathode 16 in more detail. Each mesh cathode includes two titanium filaments formed into alternating loops 20 and twists 22, in essence a chain of wire links, terminating at one end in a connector 24 and at the other in a spot weld 25. The two filaments, each 15 cm long, are formed into ten loops or links in a footprint having approximate dimensions of 1.2 cm (W)×4 cm (L). The preferred material is 0.010-inch-diameter commercially pure titanium conforming to ASTM Standard No. F-67, the same material utilized in the existing cathode of FIG. 2. However, it is utilized in monofilament form rather than trifilar form in mesh cathode 16 As can be appreciated from a comparison of FIGS. 2 and 4, the mesh cathode has a more even distribution of wire within its footprint than the trifilar wave cathode, and consequently a more uniform distribution of current to the fusion site. More specifically, it can be seen that with the trifilar wave cathode, the possible points of contact with bone are effectively limited to a curved 12-cm line because the three strands are twisted together. In contrast, the mesh cathode may contact more than twice the number of separate points in a given fusion site because it has two 15-cm filaments traversing different paths. For tissue that is not in direct contact with cathode surfaces, the mesh design allows more tissue to be in close proximity to cathode surfaces.

Figure 2:
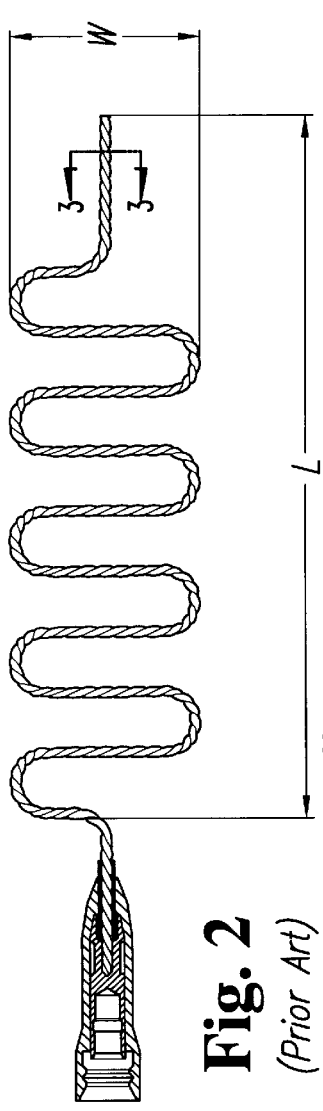
FIG. 2 is a plan view of a prior art cathode constructed of trifilar wire in a preformed sinusoidal wave shape.

As will be explained, the exposed surface area of the cathode itself is the same for the 4-cm mesh cathode and the 12-cm trifilar wave cathode of FIG. 2. Therefore, with the same applied current, the mesh cathode retains the surface area current density of a proven cathode. Surface area current density, measured in microamperes per square centimeter ($\mu A/cm^2$) of the cathode surface, is believed to be an important variable affecting the electrochemical performance of the cathode, and the above-described mesh and trifilar wave electrodes with the same surface area current density have been shown to be electrochemically equivalent in in vitro tests. Thus, the preferred geometry of a cathode according to this invention promotes an equivalent osteogenic effect along the length of each filament in the mesh structure, while providing more uniform exposure to the fusion site where the effect occurs and a lattice arrangement to guide new bone growth.

Such improvements in the delivery of direct current to a bone fusion site are provided by the disclosed mesh cathode without compromising the mechanical integrity of the cathode, even though it utilizes monofilaments rather than trifilar wire. This has been confirmed in laboratory tests involving cyclic stretching tests.

Figure 3:
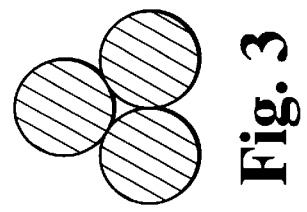
FIG. 3 is an enlarged cross-section of the cathode of FIG. 2 taken along lines 3—3.
Figure 5:
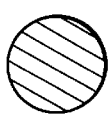
FIG. 5 is an enlarged cross-section of the mesh cathode of FIG. 4 taken along lines 5—5.

As can be appreciated from FIG. 5, the surface of each filament in the mesh cathode of FIG. 4 is entirely exposed outside of the connector except at the junctions 22, which occlude a negligible amount of the total surface area. The exposed surface area of each filament in the mesh cathode is thus effectively equal to $\pi Dl$, where D is the filament diameter and l is the total filament length outside the connector. However, since the trifilar wire cathode is made from three wire filaments twisted together, one-sixth of the surface area of each twisted filament is unexposed, as can be appreciated from FIG. 3. The exposed surface area of the trifilar wire is calculated as follows:

$$A_{exposed} = (5/6)\pi Dl$$

Consequently, the mesh cathode requires only 5/6 the total filament length of the trifilar wire cathode to have the same exposed surface area. For example, the total exposed length of filament in the 12-cm trifilar wave cathode of FIG. 2 is 36 cm, and the exposed surface area of the cathode is approximately 2.4 cm² according to the above formula. The 4-cm mesh cathode has the same surface area with two 15-cm strands totaling 30 cm of filament.

Among other embodiments, a mesh cathode with the same length footprint as the existing 24-cm trifilar wave cathode (8 cm) and the same exposed surface area is also contemplated; the 8-cm mesh cathode has two 30-cm filaments formed into twenty links. The comparative specifications of the two examples of the trifilar wave cathode and the disclosed mesh cathode, including indications for usage in spinal fusion applications, are summarized in the following table:

| Parameter | 12 cm Wave | 4 cm Mesh | 24 cm Wave | 8 cm mesh |
|---|---|---|---|---|
| Nominal Footprint [cm × cm] | 1 × 4 | 1 × 4 | 1 × 8 | 1 × 8 |
| Strand Length [cm] | 12 | 15 | 24 | 30 |
| Number of Strands | 3 | 2 | 3 | 2 |
| Total Filament Length [cm] | 36 | 30 | 72 | 60 |
| Exposed Surface Area [cm²] | 2.4 | 2.4 | 4.8 | 4.8 |
| Current per Cathode [$\mu$A] | 10 | 10 | 20 | 20 |
| Surface Current Density [$\mu$A/cm²] | 4.2 | 4.2 | 4.2 | 4.2 |
| Indicated Fusion Levels | 1–2 | 1–2 | 3 or more | 3 or more |

Figure 6:
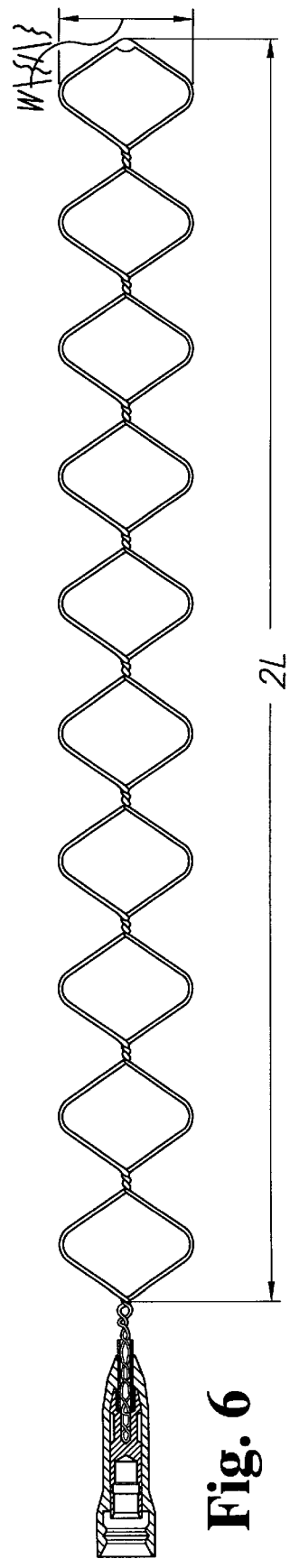
FIG. 6 is a plan view of the mesh cathode of FIG. 4 in an extended state.

As shown in FIG. 4, the width of each link 20 is nominally three times its length. The chain as disclosed can be stretched to almost four times its preformed length, although as a practical matter the attributes of a mesh are lost if the chain is stretched to the limit. FIG. 6 shows the chain stretched to twice the nominal length of its footprint, with a width W' approximately 70% of the nominal width W. As can be appreciated by inspection, the mesh cathode in its extended state still provides more even coverage of a given area with a given amount of material than the trifilar wave cathode, and thus provides a greater probability of intimate bone contact.

Figure 7:
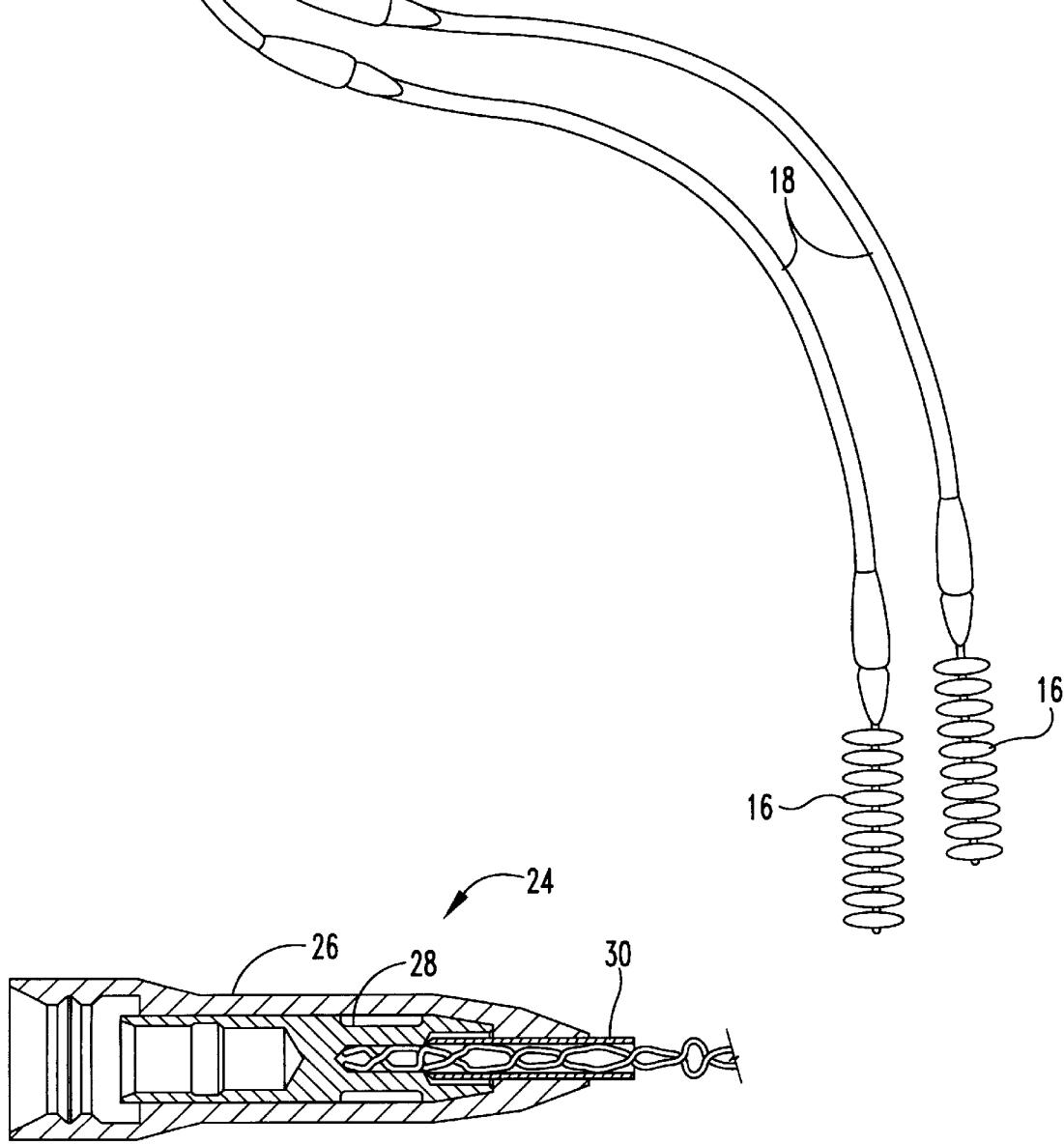
FIG. 7 is a cross-sectional side view of the connector on the mesh cathode of FIG. 4.

Turning to FIG. 7, connector 24 includes a Silastic sleeve 26 covering a titanium socket 28 that is crimped to the proximal ends of the two strands of wire forming the mesh. Silastic tubing 30 surrounds the portion of the wire strands extending through the nose of the sleeve and extends partially into the socket as shown.

Referring to FIG. 8, wire mesh for cathode 16 may be prefabricated with a set of mandrels 32 in successive translation away from a pair of wire supply spools (not shown) that supply two feed wires 34 and 36 to the mandrels as shown in the drawings. The mandrels each have a rectangular base 38 and an oval-shaped, wire-engaging upper portion 40, and they are sequentially moved into position to engage the two feed wires from the respective supply spools. Each loop 20 is formed by wrapping the two filaments 34 and 36 around the upper portion of the most recently inserted mandrel until the filaments meet, and then the two feed wires are twisted relative to the mandrels about the longitudinal axis 41 of the mesh. Each twist 22 is preferably a 540° twist, i.e., 1½ turns, and may be formed by rotating the mandrels 360° about axis 41 and simultaneously rotating the pair of feed wires 180° in the opposite direction. In this manner the mandrels have the same orientation at the start of every loop, whereby mandrel insertion and removal are simplified. The mandrels are preferably rotated clockwise after one loop and counterclockwise after the next. The wire tension is controlled during the wrapping and twisting steps by counterweighted pulleys to a level of approximately 10 ounces of force. The mandrel about which a loop has just been formed is displaced linearly by the insertion of another mandrel in the direction indicated by arrow 42, and the process of wrapping and twisting continues. Each mandrel is moved out of its wire-engaging position after several cycles of the process, as indicated by arrow 44 in FIG. 8, and may then be reinserted at the supply spool end to form another loop. The mesh so formed is taken up as raw material for final cathode assembly including attachment to a connector 24.

It is preferred to alternate the direction of twisting in order to cancel elastic reaction forces that might otherwise accumulate in one direction and cause coiling of the complete mesh about its longitudinal axis after fabrication. Thus, twisting in alternate directions facilitates the production of a planar mesh structure. Although 1½ twists have been found sufficient to support the loop shape, a single twist may be suitable in certain applications, and extra twists may be used if extra support is desired in a given application.

Figure 9:
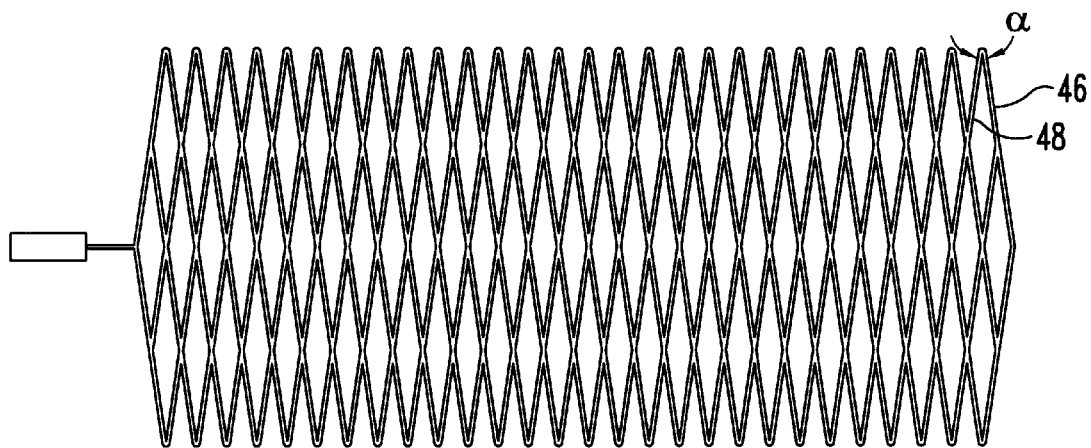
FIG. 9 is a plan view of an alternative embodiment of a mesh cathode according to the present invention.
Figure 10:
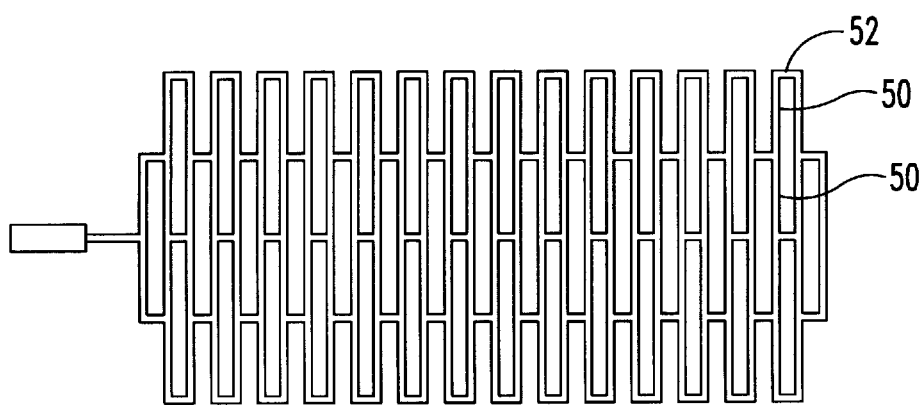
FIG. 10 is a plan view of another alternative embodiment of a mesh cathode according to the present invention.
Figure 11:
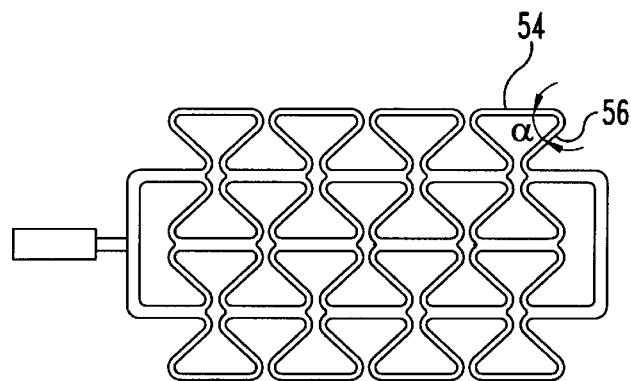
FIG. 11 is a plan view of a further alternative embodiment of a mesh cathode according to the present invention.

The mesh cathode may alternatively be formed of non-cylindrical wire, e.g., wire having a square, triangular or hexagonal cross-section. Also, although the construction with alternating loops and twists is preferred, the cathode may also be formed of thin wire segments welded or otherwise joined together without twists, such as shown in FIG. 9, or may be formed integrally such as shown in FIG. 10 or 11. The integral wire mesh may be molded, for example, or may be formed from a thin metal sheet out of which openings can be etched in a conventional manner.

Figure 12:
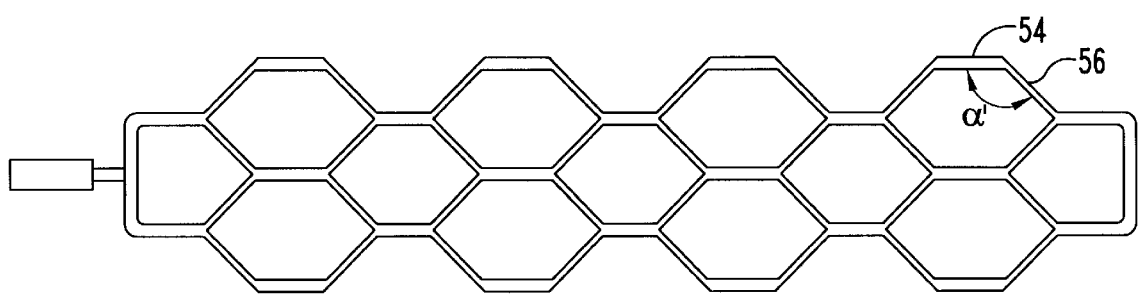
FIG. 12 is a plan view of the mesh cathode of FIG. 11 in an extended state.

The mesh cathode of FIG. 9 desirably has an included angle $\alpha$ of less than 60° between wire segments 46 and 48 such that the mesh can be stretched to more than twice its nominal length. Preferably, the angle $\alpha$ is approximately 50° such that the mesh can be stretched to twice its nominal length and still retain approximately half its nominal width. For similar reasons, the transverse wire segments 50 in the cathode of FIG. 10 are preferably longer than the axial wire segments 52 by a factor of up to about 3:1. Similarly, in the cathode of FIG. 11, wire segments 54 and 56 may be equal in length and have an included angle $\alpha$ of 45° such that, when the mesh is stretched to twice its nominal length as illustrated in FIG. 12, the included angle $\alpha'$ is approximately 135° and the width of the mesh is approximately the same as its nominal width although the axial length is doubled. Also with this embodiment, the mesh actually increases in width as it is initially stretched and remains wider than its nominal width until angle $\alpha'=180°-\alpha$.

The mesh cathode fabricated as described above reduces pre-implant preparation time with its preformed shape and yet is sufficiently flexible to conform to the shape of a fusion site and to stretch substantially in length if necessary to fit a particular fusion site, thereby minimizing pre-implant manipulations for a substantial range of bone defect sizes. It also increases the chances of intimate contact with host bone and graft material and provides a lattice to guide new bone growth. The preferred embodiment shown in FIGS. 4 and 6 is designed to be conformable to a variety of implant sites and to be flexible enough to endure cyclic deformations due to micro- or macro-motions following implantation. This design accommodates, for examples, cases of surgical spine fusion without the use of rigid instrumentation by posterior pedicle screw fixation devices. Embodiments such as those shown in FIG. 10 or 11 would be conformable to a variety of surgical sites, but may not be flexible enough to endure motions in uninstrumented bone fusion cases.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

We claim:

1. An implantable bone growth stimulator with a wire mesh cathode, comprising:

an electrical signal generator;

an anode connected to said signal generator; and a prefabricated flexible wire mesh cathode connected to said signal generator, said wire mesh cathode being extendable in length from a preformed initial length to an extended length equal to at least twice its preformed initial length.

2. The bone growth stimulator of claim 1, wherein said wire mesh cathode includes a chain of conductive wire links formed of two filaments of wire twisted together at intervals and spaced apart between the twists.

3. The bone growth stimulator of claim 2, wherein the width of each link is at least twice the length thereof.

4. The bone growth stimulator of claim 3, wherein said cathode is preformed with said links in a common plane.

5. The bone growth stimulator of claim 1, wherein said wire mesh cathode includes a chain of conductive wire links, and wherein the width of each link is at least twice the length thereof along the longitudinal axis of said chain.

6. The bone growth stimulator of claim 1, wherein said cathode includes a single chain of conductive wire links.

7. The bone growth stimulator of claim 6, wherein said links are each preformed with an axial length less than the width thereof.

8. The bone growth stimulator of claim 1, wherein said chain is formed of two filaments of wire twisted together at intervals and spaced apart between the twists.

9. The bone growth stimulator of claim 8, further comprising an electrical connector on one end of said chain for attachment to said electrical signal generator.

10. The bone growth stimulator of claim 9, wherein said wire filaments are spot welded together at the other end of said chain.

11. The bone growth stimulator of claim 10, wherein the width of each link is at least twice the length thereof.

12. The bone growth stimulator of claim 11, wherein said cathode is preformed with said links in a common plane.

13. The bone growth stimulator of claim 12, wherein said chain is formed of cylindrical wire filaments.

14. The bone growth stimulator of claim 1, further comprising an electrical connector on one end of said chain for attachment to said electrical signal generator, wherein said chain is formed of wire filaments spot welded together at the other end of said chain.

15. The bone growth stimulator of claim 1, wherein the width of each link is at least twice the length thereof.

* * * * *